(12) United States Patent
Bodduluri et al.

(10) Patent No.: US 11,771,923 B2
(45) Date of Patent: Oct. 3, 2023

(54) POSITIONING AND MOTION TRACKING USING FORCE SENSING

(71) Applicant: Zap Surgical Systems, Inc., San Carlos, CA (US)

(72) Inventors: Radhika Mohan Bodduluri, Palo Alto, CA (US); Jeffrey Schlosser, Menlo Park, CA (US)

(73) Assignee: Zap Surgical Systems, Inc., San Carlos, CA (US)

( * ) Notice: Subject to any disclaimer, the term of this patent is extended or adjusted under 35 U.S.C. 154(b) by 809 days.

(21) Appl. No.: 16/657,617

(22) Filed: Oct. 18, 2019

(65) Prior Publication Data

US 2020/0121954 A1    Apr. 23, 2020

Related U.S. Application Data

(60) Provisional application No. 62/747,626, filed on Oct. 18, 2018.

(51) Int. Cl.
*A61N 5/10* (2006.01)
*A61B 6/04* (2006.01)

(52) U.S. Cl.
CPC .............. *A61N 5/1049* (2013.01); *A61B 6/04* (2013.01); *A61N 5/107* (2013.01); *A61N 5/1067* (2013.01); *A61N 2005/1057* (2013.01); *A61N 2005/1062* (2013.01)

(58) Field of Classification Search
CPC ..... A61B 6/032; A61B 2090/065; A61B 6/04; A61B 6/0421; A61B 6/5223; A61B 6/5264; A61B 6/488; A61N 5/107; A61N 2005/1057; A61N 2005/1062; A61N 5/1067; A61N 5/1049
See application file for complete search history.

(56) References Cited

U.S. PATENT DOCUMENTS

| | | | |
|---|---|---|---|
| 6,149,643 A | * | 11/2000 | Herekar .............. A61F 9/00821 606/4 |
| 10,350,437 B2 | | 7/2019 | Fishman |
| 2004/0264640 A1 | | 12/2004 | Myles |
| 2006/0173273 A1 | | 8/2006 | Boese et al. |

(Continued)

FOREIGN PATENT DOCUMENTS

| KR | 20160025194 A | 3/2016 |
|---|---|---|
| WO | 2009067428 A1 | 5/2009 |

(Continued)

*Primary Examiner* — Christine H Matthews
*Assistant Examiner* — Joshua Daryl D Lannu
(74) *Attorney, Agent, or Firm* — Kilpatrick Townsend & Stockton LLP

(57) ABSTRACT

An array of force sensors for determining a position of an object, detecting motion of object, and tracking motion of objects in 3D space are described herein. In particular, an array of force sensors can be used to monitor anatomical motion during medical procedures, such as head motion during cranial radiosurgery, to maintain a desired alignment with the anatomical feature. Alerts can be posted to the medical machine operator and the radiosurgery system or scanner can make compensatory adjustments to maintain the desired alignment either after suspension of treatment or dynamically during treatment. Methods of detecting a position, movement or tracking motion of an anatomical feature are also provided herein.

24 Claims, 12 Drawing Sheets

(56) References Cited

U.S. PATENT DOCUMENTS

| | | |
|---|---|---|
| 2006/0215819 A1 | 9/2006 | Moyers |
| 2007/0055090 A1* | 3/2007 | Neustadter ............ A61N 5/1049 600/3 |
| 2008/0060138 A1 | 3/2008 | Price et al. |
| 2010/0246767 A1 | 9/2010 | Tanabe |
| 2011/0001622 A1* | 1/2011 | Gentry ............... G08B 21/0461 340/573.1 |
| 2011/0154569 A1 | 6/2011 | Wiggers et al. |
| 2011/0185503 A1 | 8/2011 | Yan |
| 2015/0224275 A1 | 8/2015 | Pastoor et al. |
| 2016/0175178 A1 | 6/2016 | Charles |
| 2016/0296160 A1* | 10/2016 | Larson ................. A61B 5/6892 |
| 2018/0015303 A1 | 1/2018 | Fishman |

FOREIGN PATENT DOCUMENTS

| | | | |
|---|---|---|---|
| WO | WO-2009067428 A1 * | 5/2009 | ............... A61B 6/04 |
| WO | 2012056397 A1 | 5/2012 | |
| WO | 2017063084 A1 | 4/2017 | |
| WO | 2019016735 | 1/2019 | |

* cited by examiner

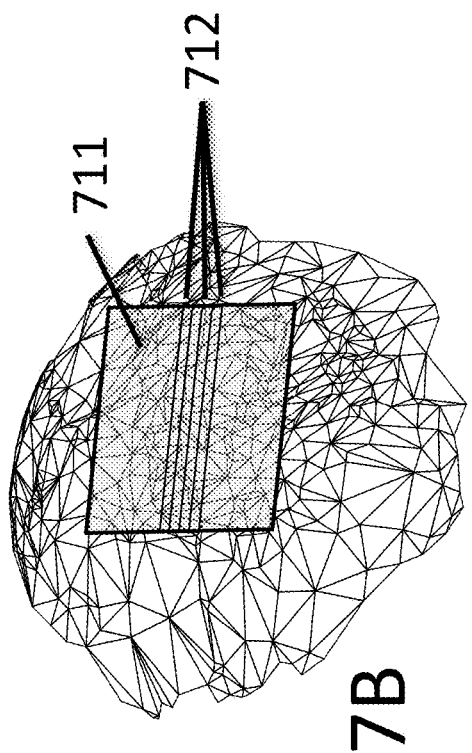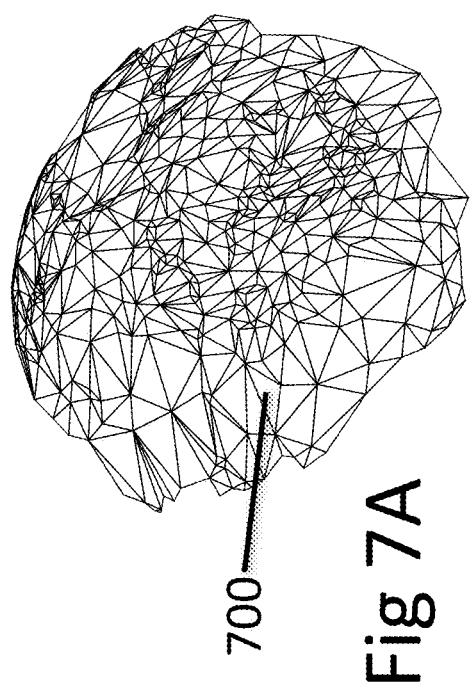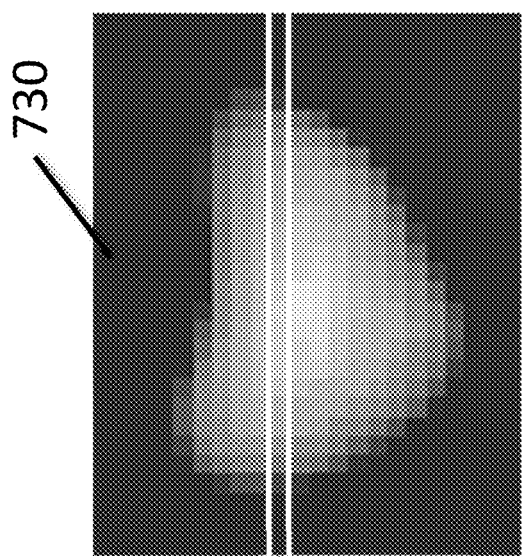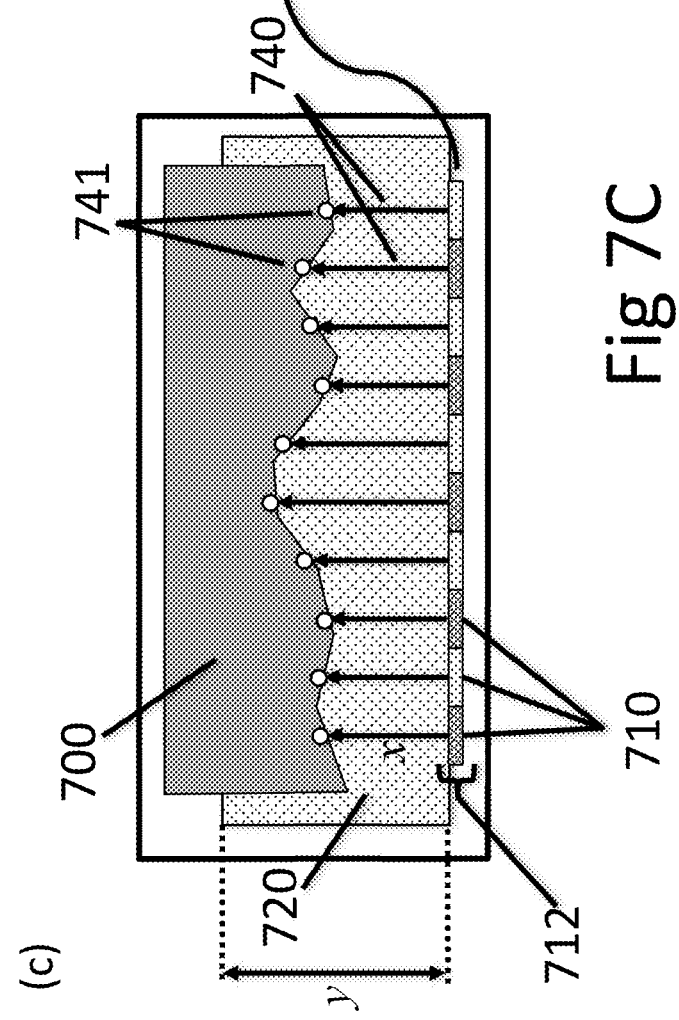

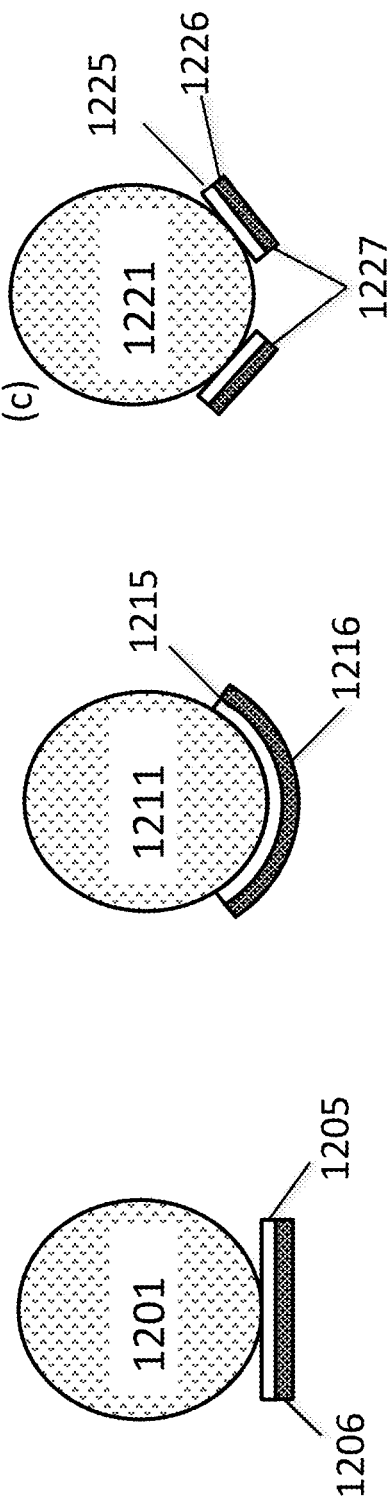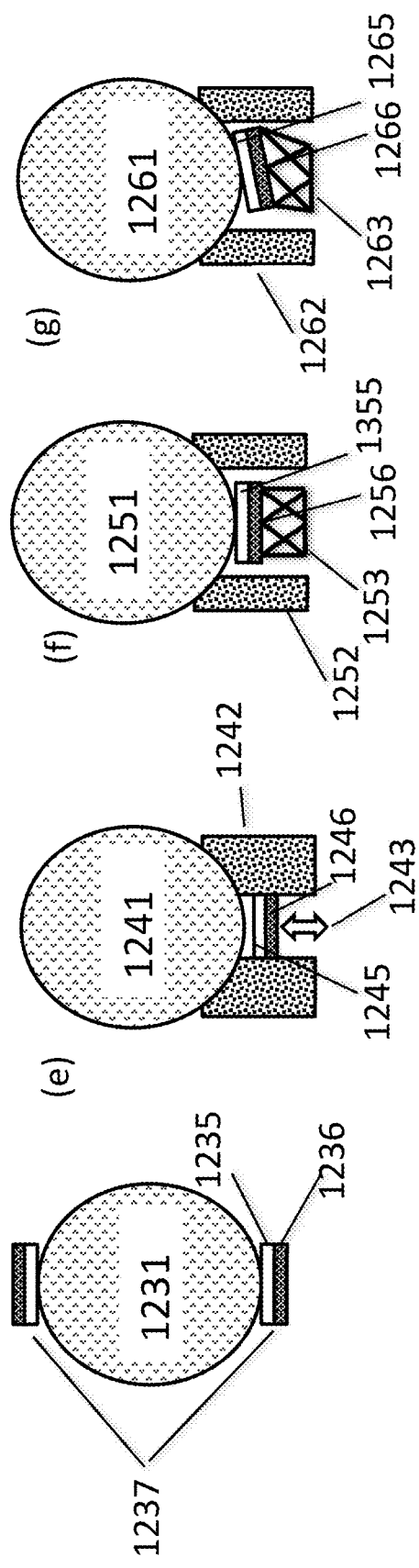

POSITIONING AND MOTION TRACKING USING FORCE SENSING

CROSS-REFERENCES TO RELATED APPLICATIONS

The present application claims the benefit under 35 USC § 119(e) of U.S. Provisional Appln. No. 62/747,626 filed Oct. 18, 2018; the full disclosure which is incorporated herein by reference in its entirety for all purposes.

FIELD

The present invention relates generally to the field of positioning and motion tracking, in particular, computerized surgical navigation, robotic medical treatments and stereotactic radiosurgery.

BACKGROUND OF THE INVENTION

When performing computerized surgical navigation or computerized stereotactically, or image-guided guided procedures including stereotactic radiosurgery, the computer's model of the location of the surgical anatomy is assigned a location in both virtual and real space. If the patient moves or is moved, and this change in location of anatomy is not accounted for, the procedure can be misdirected, potentially producing deleterious results. Therefore there are at least two strategies that have been used to deal with movement.

The first strategy includes preventing movement entirely by fixing the patient (for example their head) in place with fixation means such as a stereotactic frame or Mayfield head holder. This approach of rigid fixation is also used with the Gamma Knife (Elekta, Stockholm, Sweden). Disadvantages of this approach include significant discomfort for a patient, whose head must be fixed in place with metal screws, and a cumbersome setup procedure.

The second strategy includes tracking the movement of the head and shifting the computer's representation of the location of the pertinent anatomy and mechanically correcting with the actuator (e.g. radiosurgical device) accordingly. The latter has typically been performed in the context of stereotactic radiosurgery by using image based tracking: determining location in space by use of visible, infrared light, or x-rays. Devices for tracking known in the art include the infrared Polaris system (Northern Digital, Waterloo, Ontario Canada), the x-ray based tracking system of the Cyberknife (Accuray, Inc., Mountain View, Calif.), the MRI based tracking system of the ViewRay (ViewRay, Inc., Oakwood Village, Ohio), and the visual surface based tracking system AlignRT (Vision RT, Ltd., London, UK). When tracking is employed, the stereotactic device needs means for reacting to and correcting for the detected position change. Such devices include the Cyberknife robotic arm (Accuray, Inc., Mountain View, Calif.), the RoboCouch for CyberKnife (Accuray, Inc., Mountain View, Calif.), most radiotherapy couches with 5-6 degrees of freedom, and electronically positionable surgical tables.

A disadvantage to the tracking approach is that they require costly, time consuming image capture which can (in the case of x-rays) expose the patient to additional ionizing radiation each time a radiograph is taken. Furthermore, if the treatment modality is X-rays, the therapeutic X-rays need to be stopped in order to use the diagnostic-intensity X-ray position-tracking because the signal received by this latter low-radiation-dose detectors would otherwise be swamped by the much higher-dose therapeutic-intensity X-ray used to treat the patient. There is a need for a low-cost and continuous method for tracking the position of a patient's head and body during computerized and robotic stereotactic procedures.

SUMMARY OF THE INVENTION

The invention described herein pertains to systems and methods for positional and/or motion tracking of an object and have particular applicability to determining anatomical movement in a patient undergoing a medical procedure. In some embodiments, the invention pertains to systems and methods for determining the position and motion of a patient's head using force sensing. In some embodiments, when a sensed threshold is passed indicating that head movement has occurred, the therapy is paused, and re-registration with the original treatment plan is achieved by means known in the art such as taking another radiographic image of the skull. In another embodiment, the pressure pattern created by the weight of the patient's head on a sensor-laden pad describes the new 6 degree-of-freedom (DOF) position of the patient's head relative to its initial position, and compensatory re-registration may be accomplished directly and automatically. In yet other embodiments, the pressure pattern can be used to localize the absolute 6 DOF position of the patient's head in 3D space, thus eliminating the need for using other imaging modalities to register the initial position of the patient's head. Throughout this disclosure, the terms "touch" "pressure" and "force" are used interchangeably to describe the amount of force exerted on a force-sensing element. In one aspect, the invention is pertinent to rigid body tracking and any associated use. In some embodiments within the medical context, the position of the internal target anatomy is identifiable as it assumed to be in a generally fixed location relative to the external anatomy, for example, a target within the head or a portions of the limb, which would be tracked separately. It is understood that the positions of targets within certain internal organs may change relative the external abdomen such that any changes would need to be separately determined and accounted for. While various position and motion tracking features are described herein in regard to medical treatments, in particular stereotactic radiation delivery, it is understood that these same concepts can be used in any medical procedure in which precision or semi-precision tracking of a body part is desired, which includes non-radiation based stereotactic surgery. It is further appreciated that these concepts can apply to rigid-body tracking or tracking of a position or motion of various other objects or anatomies for various other purposes, including non-medical applications, for example detailed imaging or mapping.

In one aspect, methods of tracking a position or motion of a targeted tissue for a medical treatment are provided herein. It is understood that these methods have particular applicability to stereotactic medical or surgical procedures (with or without radiation) but can also apply to various other procedures or non-medical purposes in which position or motion of an object (e.g., a resting head, portion of a body) is desired. Such methods can include steps of: determining a force or pressure distribution from one or more force sensors engaged, directly or indirectly, with a portion of the patient's body having the targeted tissue; and determining a change from an initial position of the portion of the patient's body, in which the targeted tissue is aligned with a radiation treatment beam from a radiosurgery system, by detecting a change in the force or pressure distribution detected with the one or more force sensors. Based upon the detected changed, transmission of the radiation treatment beam can be suspended and/or adjusted. In some embodiments, the methods then determine an updated position of the portion of the patient's body having the targeted tissue, and re-align the radiation treatment beam with the targeted tissue and resume transmission of the radiation treatment beam if needed.

In some embodiments, the change in force or pressure distribution comprises the detection exceeding a pre-defined threshold. A notification indicating the change from the initial position can be output to a user. In some embodiments, determining the updated position of the portion of the patient's utilizes an imaging procedure native to the radiosurgery system (e.g. obtaining a radiographic image that is matched to a digitally reconstructed radiograph (DRR) image). In other embodiments, the methods includes determining the updated position of the portion of the patient's body based, at least partly, on a detection output from multiple force sensors disposed within an array. The updated position can be determined based on any of: outputs of the force sensors, relative positions of sensors within the array, and a material property of a deformable material in which the sensors are disposed, or any combination thereof.

In another aspect, motion tracking system for tracking a targeted tissue for a radiation treatment are provided herein. Such systems can include one or more force sensors arranged for detection of a force or pressure distribution associated with a position or movement of a portion of the patient's body having the targeted tissue, and a processor configured to: determine a change from an initial position of a portion of the patient's body, in which the targeted tissue is aligned with a radiation treatment beam from a radiosurgery system, by detecting a change in the force or pressure distribution with one or more force sensors and suspend transmission of the radiation treatment beam upon the detected change or adjust the treatment beam upon the detected change. Adjusting the treatment beam can include adjusting the trajectory, shape or intensity of the beam treatment beam upon the detected change. This may be accomplished by adjusting aim of the linear accelerator and collimator, or by stereotactically repositioning the patient by movement of the patient table. The system can be further configured to notify a user of the detected change or to determine an updated position of the portion of the patient's body having the targeted tissue and re-align the radiation treatment beam with the targeted tissue before resuming radiation treatment beam of the targeted tissue. Such systems can be configured with programming to perform any of the methods and procedures for motion tracking described herein. In some embodiments, the one or more sensors comprise at least one strain gauge extending between a treatment mask and a patient support. In other embodiments, the sensors comprises a sensor array having multiple sensors disposed under or extending partly about the portion of the patient's body having the targeted tissue. In some embodiments, the systems include an interface member between the patient and the sensors having one or more protruding features at known locations to provide improved resolution of a force image obtained from the sensor array. In some embodiments, the system is configured to determine an updated position of the portion of the patient and command one or more actuators to adjust a therapy system or a patient support to facilitate re-alignment with the targeted tissue In yet another aspect, the system and methods are configured to dynamically adjust the treatment beam based on a detected change. It is appreciated that such systems and methods can utilize any of the features described herein. It is further appreciated that, in any of the embodiments herein, adjusting the treatment beam can include any of: adjusting the direction of the treatment beam, adjusting the shape of the beam, adjusting the intensity of the beam, adjusting the position of the patient by moving the patient table, or any combination thereof.

BRIEF DESCRIPTION OF THE DRAWINGS

FIGS. 7A-7C describe the process by which force simulation is used to characterize the pressure that is produced on a pad by a given shape and position of the tracked object.

FIGS. 12A-12G demonstrate examples of different configurations of the sensor arrays and headrest.

DETAILED DESCRIPTION

Figure 1:
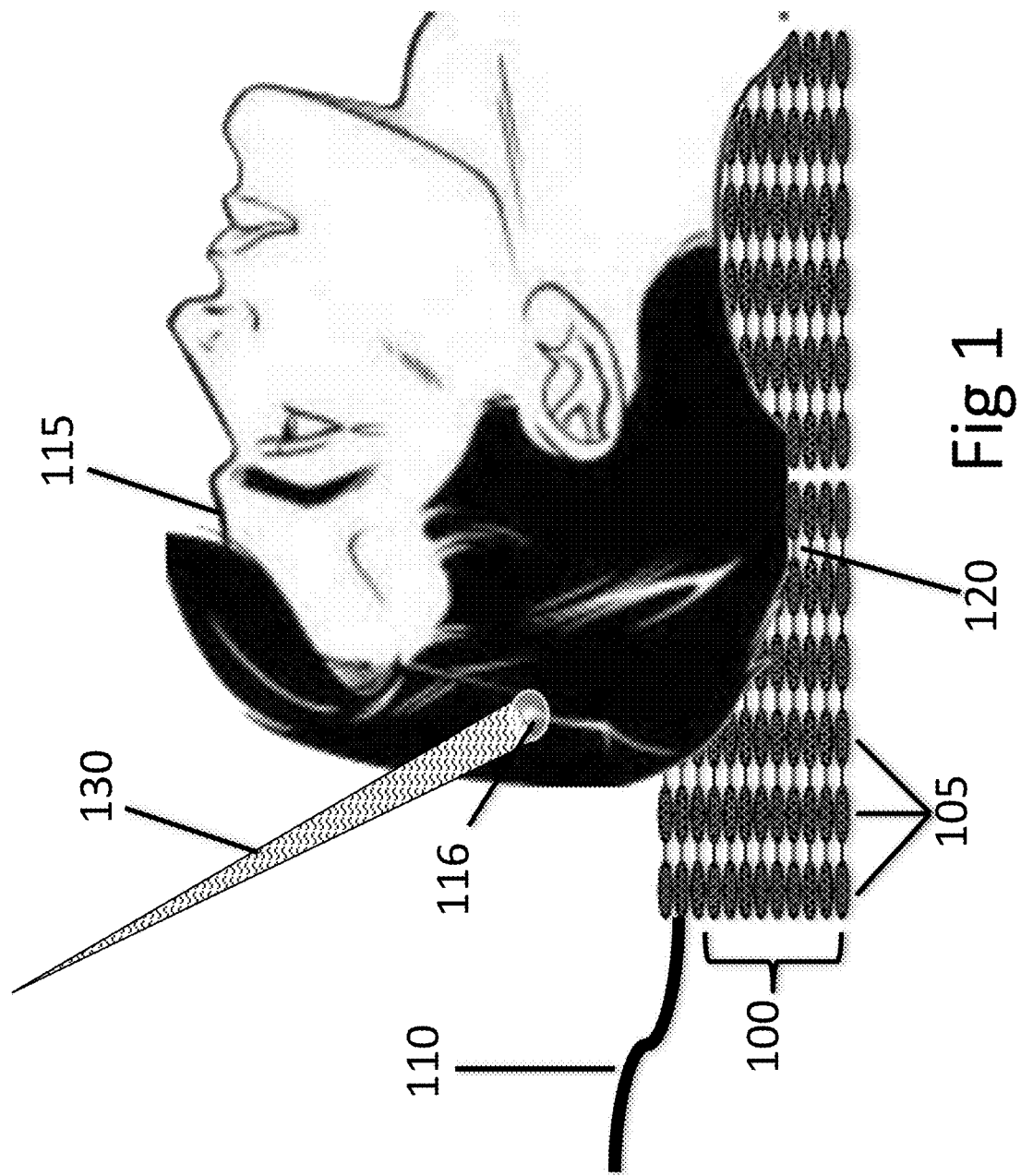
FIG. 1 shows an example embodiment in which the patient's head rests on the multi-pressure-sensor array matrix of the pad.

Two general modes of operation are described in the context of the present invention: A) thresholding that determines that a movement has occurred, and stopping treatment until the position can be reassessed and compensatory movements made in the effector before resuming treatment; B) inference of a new 6 DOF position, then cuing compensatory movement in the effector before resuming treatment. It is appreciated that various other modes can utilize the concepts of one or both of these modes alone or in combination.

As will be detailed, in Operating Mode A detection of movement may be as simple as detecting change of force on a single strain gauge, or the change of sensor readings on a force-sensing matrix, for example using matrix subtraction or cross correlation. In thresholding, a simple determination is made that movement has or has not occurred. In this case there is no particular inference in terms of what the new position of the head is. In the case of stereotactic radiosurgery, detection of a movement may trigger a series of automated steps, for example: 1) immediately stopping the delivery of radiation beams, 2) determination of the new position by standard means such as taking a new radiographic image which is matched to a digitally reconstructed radiograph (DRR) image by means native to the radiosurgery machine and as is known in the art, and 3) movement of the radiosurgery beam delivery system or the patient to compensate for the new position of the head by means. Such compensating movement of the radiosurgery beam can be according to a procedure native to the radiosurgery machine, including any compensating approaches that are known in the art. Once the patient's head a re-aligned properly with the beam, one or more new reference force readings are established and force sensing is resumed.

In Operating Mode B, the position of a patient is inferred from patterns of activation of one or more sensor elements, typically force sensor elements. Here, the new position of the patient as computed from the sensor elements will be used to determine how the treatment effector, for example a radiosurgical system, adjusts its trajectory for the next beam delivery, or adjust the position of the patient for the next beam delivery, such as by movement of a patient table. Likewise a robotic or stereotactic surgical system will accordingly adjust the physical trajectory of instruments, the computerized view of the anatomy, or the physical position of the patient. Mode B will be described in terms of detecting the position and orientation of a body with a force sensor. In general, position and orientation of the body is determined by the force magnitudes output by the one or more force sensor elements, the respective locations of the sensor elements in 3D space, and the material properties of the material coupling a respective force sensor with the body of interest. In some embodiments, a deformable/compressible material coupled between the force sensor and the body transmits force to the sensor elements according to how much the material is deformed (see for example FIG. 5). When the material properties of the deformable material are known, a mechanics model may be used to determine the position and orientation of the body of interest as a function of the aforementioned sensor readings, positions, and mechanics model. In some embodiments, the compressible coupling medium can be the patient's scalp and the body of interest can be the patient's skull. In other embodiments, the body of interest can be a rigid geometrically-known synthetic object and the deformable material can be rubber or foam. The synthetic body may in turn be coupled to the patient's head in order to provide tracking for cranial radiosurgery. While the examples of Operating Mode B utilize force sensor elements, it is appreciated that various other types of sensors can be utilized in a similar manner, for example, displacement sensors that can detect a displacement of portions of the patient's head or the compressible material or any type of sensor that can correlated to a force or change in force by the body of interest. As described herein, the force is exerted by the weight of the body of interest.

In Operating Mode B, the position of the patient may be inferred during treatment relative to its initial position at the start of treatment. Alternatively, the position of the patient may be determined in absolute 3D space relative to the treatment device without reliance on another positioning modality. At least three different methods for positioning and tracking the patient may be employed in Mode B: Digitally Reconstructed Force Matching (DRFM), Point Cloud Matching (PCM), and Control Point Matching (CPM), each of which are described in detail below.

The present invention can involve force sensors placed in a variety of locations under, on, and around the portion of the body or the object that one wants to assess for movement or position. For head positioning and tracking, such configurations can include a flat sensor array beneath the head (a), a flexible sensor array beneath the head (b), two or more arrays placed on either side of the head (c), a sensor or sensor arrays in front of the head and along the back of the head (d), among others. In some embodiments, sensors may be located in front of or behind a treatment mask used to partially immobilize the patient. Such a treatment mask can be linked to a lever arm which mechanically amplifies the effect of subtle movements. In some embodiments, sensors are located on a linear motion platform (e) which applies a programmed amount of pressure on the patient's skin to ensure a comfortable treatment experience and to ensure that the force sensor readings are not saturated due to excessive force from the anatomy. In another embodiment, a multi-degree-of freedom robotic apparatus (f) may be used to shift the force sensors(s) with respect to the patient's head or body in a predesignated manner as to allow determination by the system of a relationship between head position and force patterns on a sensor matrix prior to an actual medical procedure. An example of such apparatus could be a 6 DOF Stewart platform or a 2 DOF apparatus that controls only the pitch and yaw of the force sensor.

FIG. 1 shows an example embodiment in which the patient's head 115 rests on a multi-pressure-sensor array matrix, which may be incorporated into a pad or pillow, so that a radiation therapy beam 130 can be aligned with a target tissue 116 (e.g. tumor) in a portion of the patient's head 115 for therapy. It is appreciated that the position orientation of the target tissue 116 can be readily determined from the position and orientation of the associated portion of the patient (e.g. patient's head). Multi-sensor pad 100 is composed of numerous pressure sensor elements 105. These elements may use piezoelectric, resistive, capacitive, optical, pneumatic, hydraulic sensing, or any suitable sensor utilizing any other method of pressure/force sensing known in the art. In a preferred embodiment, the sensor matrix is the Morph by Sensel (Mountain View, Calif.). The Sensel has approximately 20,000 pressure sensor elements, each with a force range of approximately 5 g-5 kg, which may be queried at a rate of approximately 125 Hz (8 ms latency).

Signal cable 110 relays information from the sensor matrix pad to an external computer or electronic device for pressure pattern and location interpretation. Patient 115, preferably lying supine on a treatment table, rests their head on multi-sensor pad 100, putting pressure on region 120 of multi-sensor pad 100. In actual use, the patients head will typically be surrounded on the sides by a custom formed headrest, such as the Accuform Headrest (CIVCO Radiotherapy, Coralville, Iowa), with a cutout on the lower margin to permit the back of the head to rest upon the pad. Also in actual use, the patient's face will typically be within a custom-formed facemask such as the Aquaplast facemask (Qfix, Avondale, Pa.), which is affixed to the table, substantially reducing the amount the patients head can move. In an alternative embodiment, multiple sensor pad surfaces may be placed under and beside the head, exposed via cutouts or open windows formed in the headrest of face mask inner surfaces.

Figure 2:
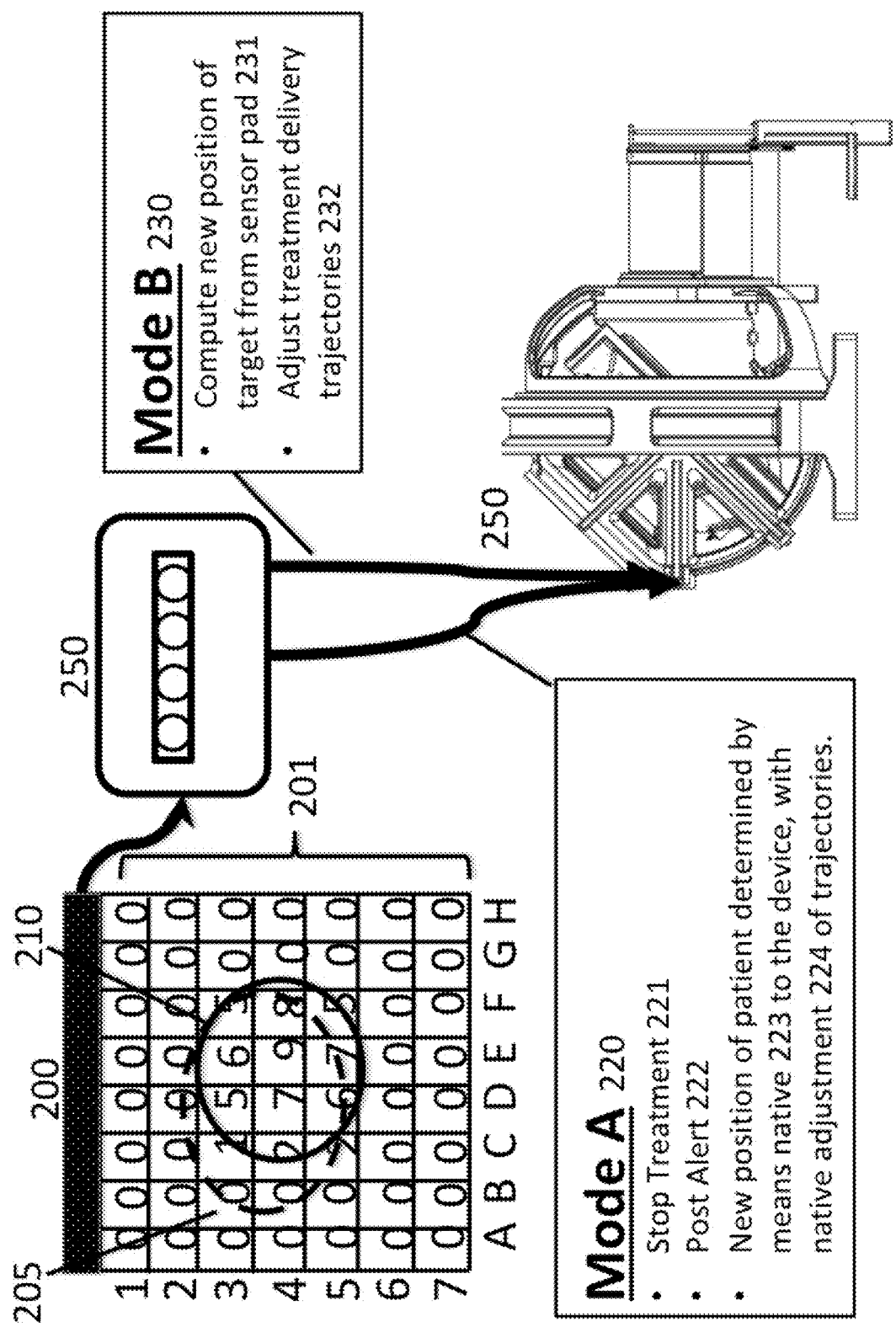
FIG. 2 illustrates a multi-pressure-sensor matrix on a pad functioning in two modalities: A) threshold detection of movement versus B) 6DOF position and motion tracking.

FIG. 2 illustrates a matrix 201 of force sensors 200 that can be incorporated into a pad on which the patient's head rests. In this embodiment, the force sensor matrix can function in two modalities: A) threshold detection of movement versus, and B) 6DOF positioning and motion tracking.

On the matrix of force sensors 200, each sensor is shown, for illustration purposes, with an example downward force reading on a scale of 0 to 9. It is appreciated that this is but one example, and in other embodiments, the matrix may utilize force sensors that discriminate thousands of levels of downward pressure. Force is detected from the occuput of the patients head in one time period at an initial time, for example group of sensor elements 205, and at a later time, for example group of sensor elements 210. The force readings from sensor matrix 201 are relayed to microprocessor 250 of the computer system, where an output determination Mode A 220 versus Mode B 230 is made. In Mode A 220, a thresholded determination is made as to whether or not patient movement has occurred. If it is determined that movement has occurred, by exceeding a pre-defined threshold, the output instructs the effector system to stop 221, post an alert 222 to the user, and use its native means 223 to determine the new position of the patient, and native means to adjust trajectories 224 to the new position of the patient. In the case of stereotactic radiosurgery system 250, this means that upon detection that movement above a certain threshold has occurred, the treatment beam, if active, will immediately stop 221, an alert 222 that movement has occurred will be posted to the user (typically a radiosurgery technician). At this point, the a radiosurgery system uses its native means, for example taking radiographs for the purpose of tracking the new position of the patient's head. Radiosurgical system 250 then typically takes new radiographic images for the purpose of head tracking adjusts beam trajectories 223 or adjusts the table position to compensate. For example, if the patient has moved their head to the right, the system may move a robotic patient table to the left in order to bring the target within the patient's head back to center. By contrast, operating in Mode B 230, the system directly computes the new position of the patient's head 231 from the sensor matrix 200, stops the current beam, and adjusts 232 treatment trajectories accordingly. In some embodiments, this process if performed automatically. Force sensing matrix 200 may be covered by a thin cushion pillow so long as the effect of the head's weight upon the pressure sensor elements is not excessively diffused.

Figure 3:
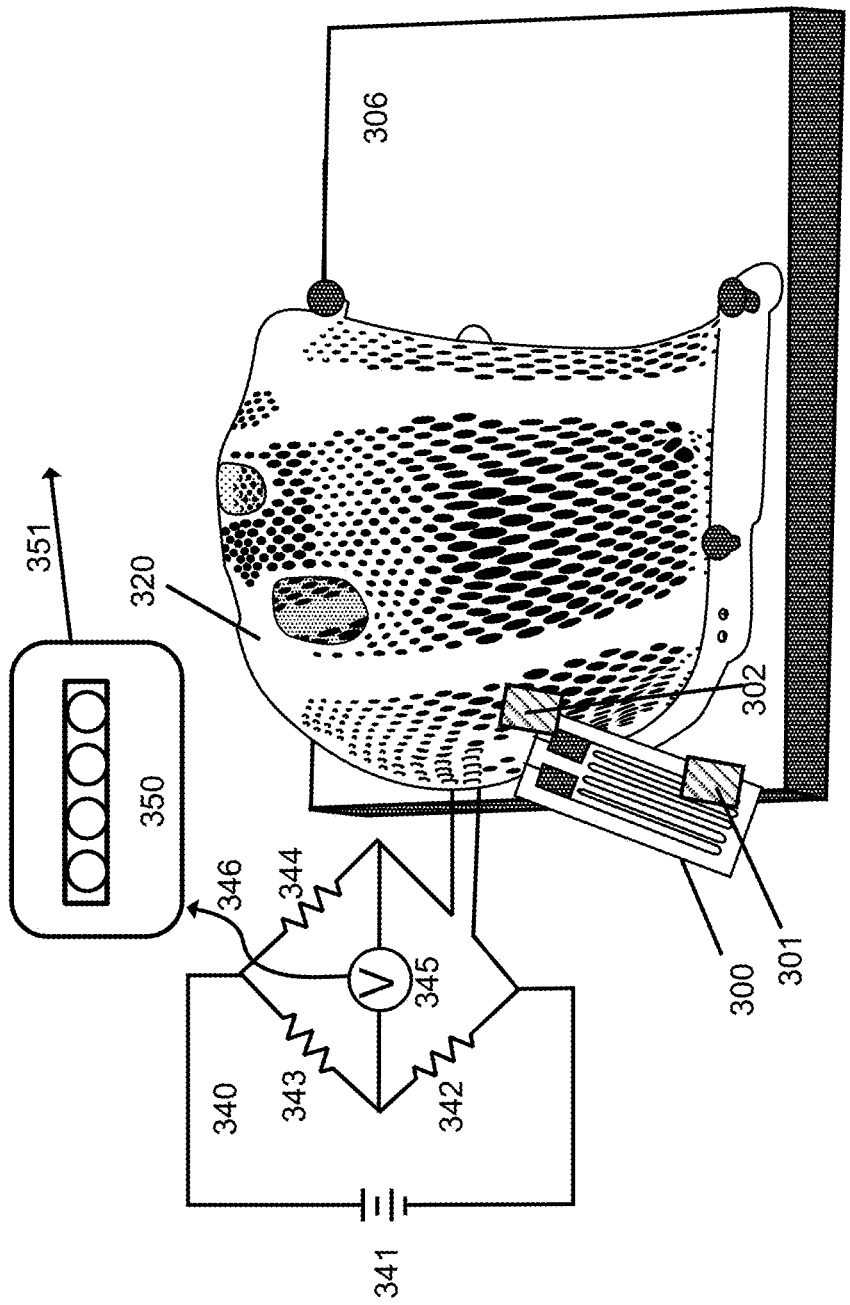
FIG. 3 is an illustration of threshold detection by a strain gauge affixed between a radiosurgery mask and the treatment table in Mode A.

FIG. 3 is an illustration of threshold detection (Mode A) in its simplest form, in which there is a single force sensor, here in the form of strain gauge 300. Strain gauge 300 is affixed by connectors 301 and 302 between a radiosurgery mask 320 and the treatment table 306. Strain gauge 301 may also be placed underneath the patient's head, or at other locations around treatment table 306 and treatment mask 320 that register movement of a patient's head. Strain gauge 300 may be electronically supported by a two-wire Wheatstone quarter-bridge circuit 340 composed of power supply and return 341 and resistors 342, 343 and 344 that produce a voltage 345 that is relayed by connector 346 to processor 350. Because both leads of the strain gauge 300 are located between adjacent corners of the bridge circuit 340, and a deformation of the strain gauge changes the resistance across it, the bridge arm resistance becomes the sum of the three resistors 342, 343 and 344, causing a lack of symmetry and a consequent voltage 345 across the center and output 346 to processor 350. Other supporting circuits are known in the art and may be used. In its simplest form, processor 350 may be a voltmeter with threshold determination and determination output means 351. A signal is sent via output 351 which triggers the processes denoted as Mode A in FIG. 2. In some embodiments, multiple force sensors may be used at various locations on the treatment mask.

Figure 4:
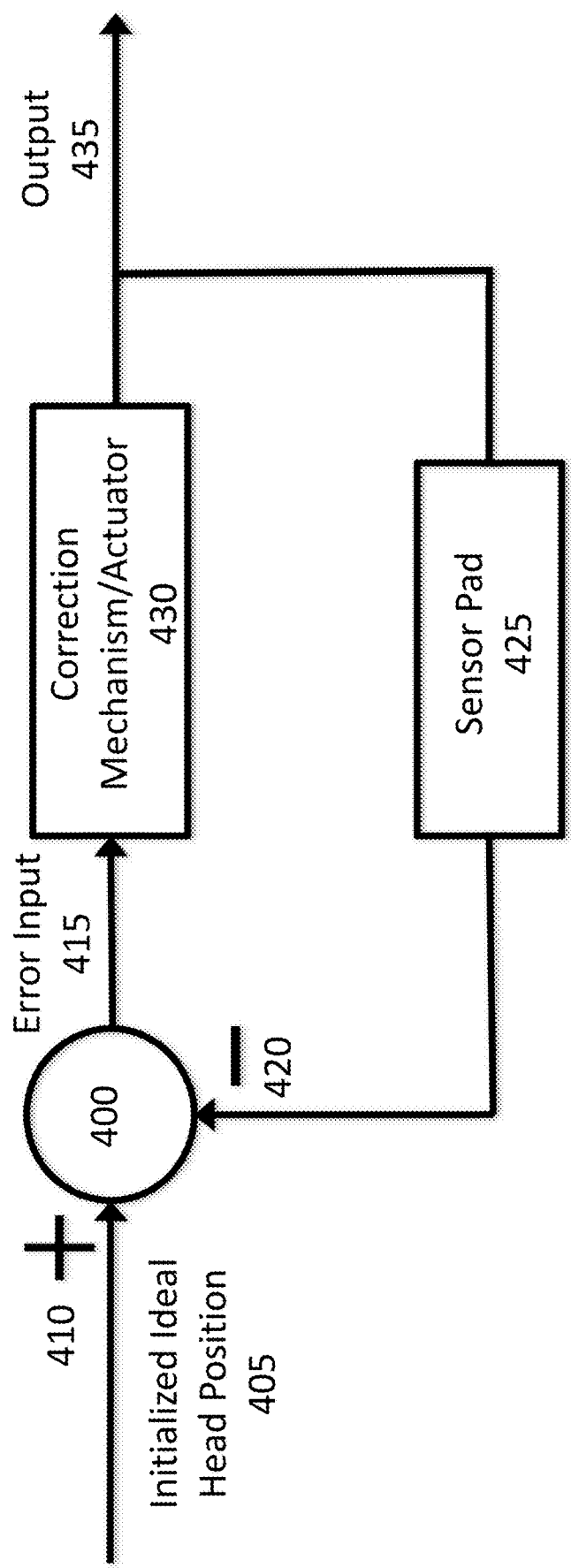
FIG. 4 is a schematic of the computerized control process by which reading by the head pressure sensor pad translate into corrective movement in the actuator device in Mode B.

FIG. 4 is a schematic of the general computerized control process by which a reading by the head pressure sensor matrix translates into corrective movement in the actuator device, for example a radiosurgical system. The initialized ideal position of the head 405, is achieved by manual positioning and initial calibration of actuator devices such as radiosurgical machines and motorized multi-axis patient tables, and is received by computing device 400 as input 410. If the head pressure sensor pad indication 420 is that the patient's head has remained in that ideal position 405, error input 415 is 0 and no action ensues from computing device 400. If ideal position 405 is not indicated by sensor pad 425, an error signal 420 will be input to the computing device, an error input 415 will be sent to the computer controls of correction mechanism/actuator 430. Correction mechanism/actuator 430 may be, for example, built in to radiosurgical device, or a motorized multi-axis patient table. Movement of correction mechanism/actuator 430 serves, for example, to bring the surgical actuator (e.g. radiosurgical collimator) aim back into appropriate alignment with the intended target tissue (e.g. tumor in a portion of the patient's head), and is received as output 435 by the system before proceeding with transmitting therapy to the target tissue.

Figure 5:
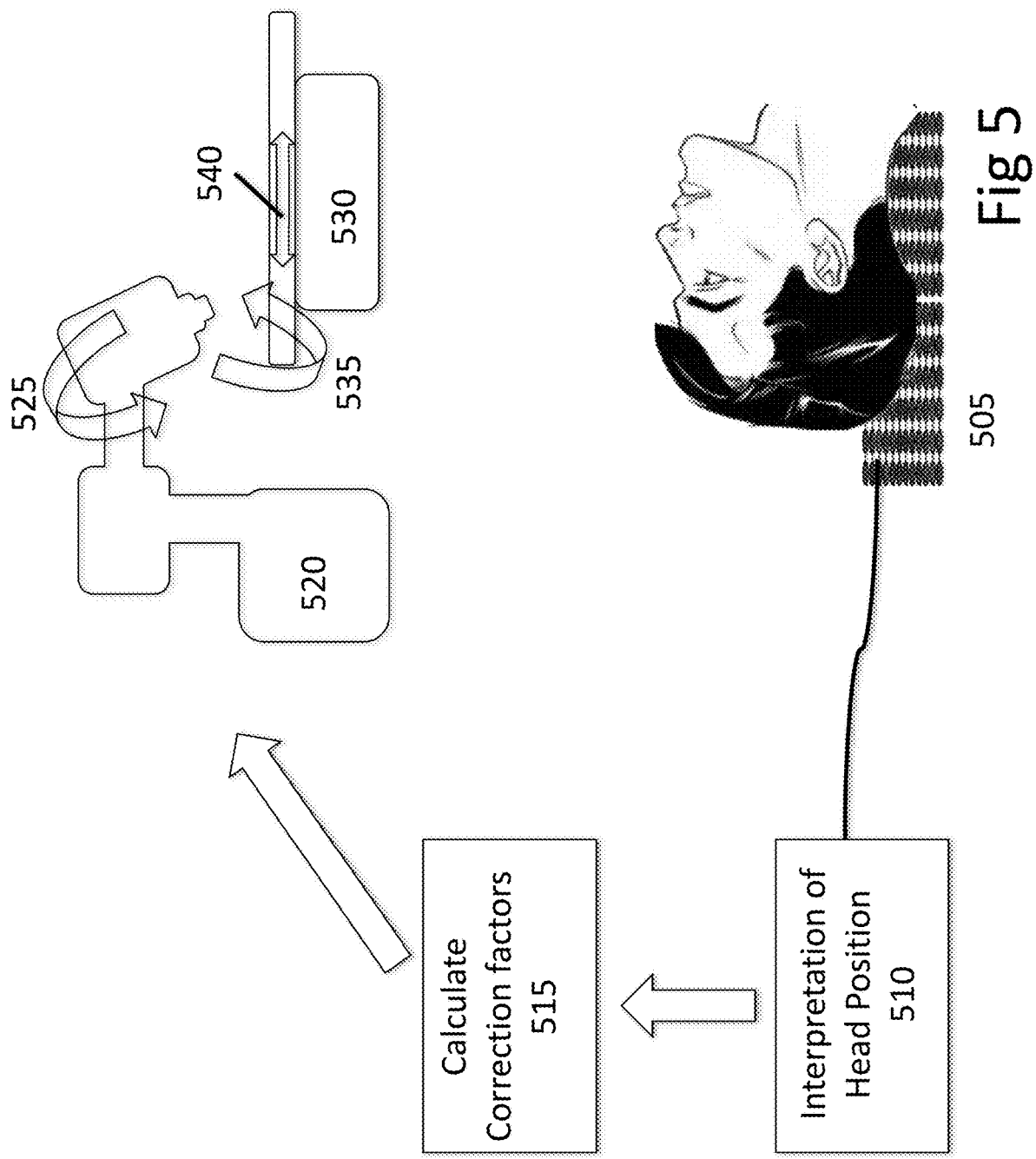
FIG. 5 illustrates an overview of the process by which head pressure is used to control the aim a radiosurgical machine and position of a patient table.

FIG. 5 provides an overview of the process by which the pressure from the weight of the patient's head is interpreted and used to control the aim of a radiosurgical machine and/or a position of a patient table, in accordance with Mode B of FIG. 2. Sensor matrix 505 registers the force pattern upon it from the patient's head. The location or position of a patient's head is determined by computing device 510, and spatial correction factors for the actuator device are calculated by computing device 515. If the head position does not correspond with the ideal position, these signals are relayed to actuator device radiosurgical machine 520 and/or motorized multi-axis patient table 530. As a result, radiosurgical machine 520 may be repositioned 525 to compensate and/or motorized multi-axis patient table 530 may be pitched and rolled 535, or translated 540 to compensate and bring the patient's head back into proper alignment with respect to radiosurgical machine 520.

Figure 6:
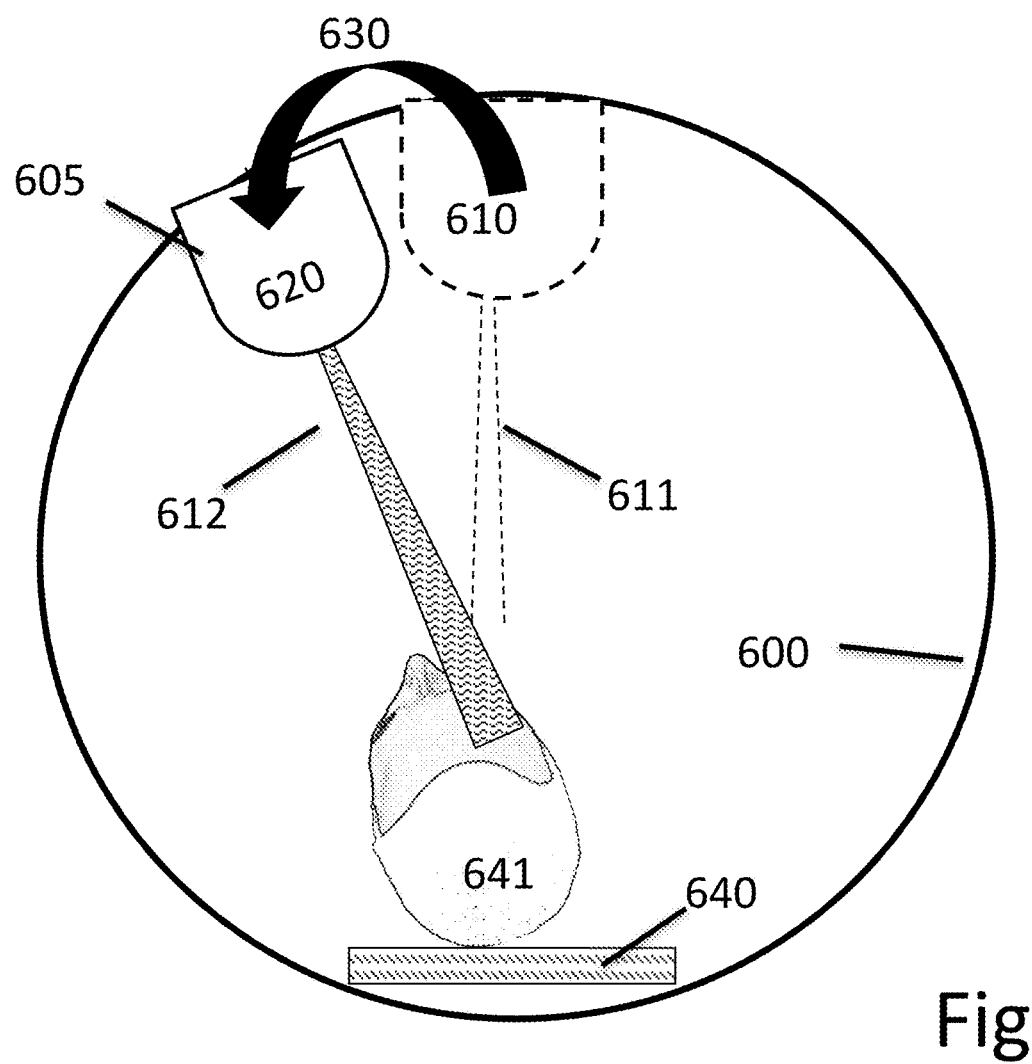
FIG. 6 illustrates the compenatory movement of an isocentric radiosurgery machine in response to a head motion interpetation (Mode B).

FIG. 6 illustrates the compensatory movement of an isocentric radiosurgery machine in response to head motion interpetation in Mode B. The inner surface of gantry 600 holds within it sensor matrix 640, patient's head 641, linac 605 in former position 610 producing beam 611 and linac 605 in present position 620 producing beam 612. It will be appreciated that as patient's head 641 has rolled to the left, a compensatory movement occurs to linac 605 to bring beam 612 onto target in patient's head 641. Such compensatory movement may be achieved by either Mode A or Mode B shown in FIG. 2.

FIGS. 7A-7C describes the process by which force simulation is used to computationally predict the pressure that is produced on a series of sensor elements by a given head shape and position. This process is fundamental to the DRFM and PCM algorithms detailed in FIGS. 8A-8B and FIGS. 9A-9D, as will be described in sections below. As the first step in force simulation, a model of the tracked object 700 is produced. In the case of tracking the skull in cranial radiosurgery, the planning CT scan can be used to produce a model of a portion of the skull surface that is coupled to the force sensor elements. In some embodiments, the model is a rigid triangle surface mesh. Standard techniques known in the art may be used to derive the rigid triangle surface mesh from the segmented skull voxels of the CT scan. The next step in DRFM is to establish the 3D location of the force sensor elements with respect to the tracked object. In some embodiments, the individual force sensor elements 710 are arranged in a flat matrix array 711 which consists of a series of sensor element rows 712. Next, the force reading of each sensor element is simulated using a model of how the deformable material 720 transmits force to each sensor element. The result is a simulated map 730 of the force magnitude sensed by the sensor elements.

In some embodiments as shown in FIG. 7C, the deformable material model for the force simulation is a linear spring model. The amount of force transmitted to each sensor element is computed by finding the normal distance of each respective sensor element to the rigid triangle object mesh. The normal distance may be found by finding the intersection point 741 of the sensor normal vectors 740 with the triangle mesh 700, then computing the linear distance between the sensor element 710 and the intersection point. The distance x is then subtracted from the nominal resting position of the deformable material y and multiplied by a spring constant k (e.g. elasticity) to arrive at the sensor element force F as follows: $F=(y-x)*k$. In FIG. 7C, each row 712 of the force sensor array 711 is simulated and contributes to one row of the resulting force simulation map matrix 730. In other embodiments, a more sophisticated deformable material model is implemented. For example, a finite element analysis (FEA) model can be used to simulate the force transmitted to the sensor elements by dividing the deformable material into discrete finite elements, applying known material properties to the elements, computationally deforming the material according to the shape of the rigid object mesh, then using standard FEA techniques to compute the force transmitted to each sensor element.

In some embodiments, the force simulation may incorporate additional properties of the force sensing elements in order to produce a more faithful simulation of the actual force measured by a real-world sensor. For example, a matrix array of force sensors 711 may respond to a pinpoint force input with a point spread function (PSF) with finite gaussian spread (similar to a traditional x-ray PSF) because of the way the array elements are manufactured and coupled together on a substrate. The force sensor array PSF effectively results in a blurred force "image" 730 in accordance with the variance of the spread. The aforementioned force simulation may include an additional step of convolving the force image with a gaussian kernel of appropriate spread in order to more accurately represent the real-world force measured by the array.

Figure 8:
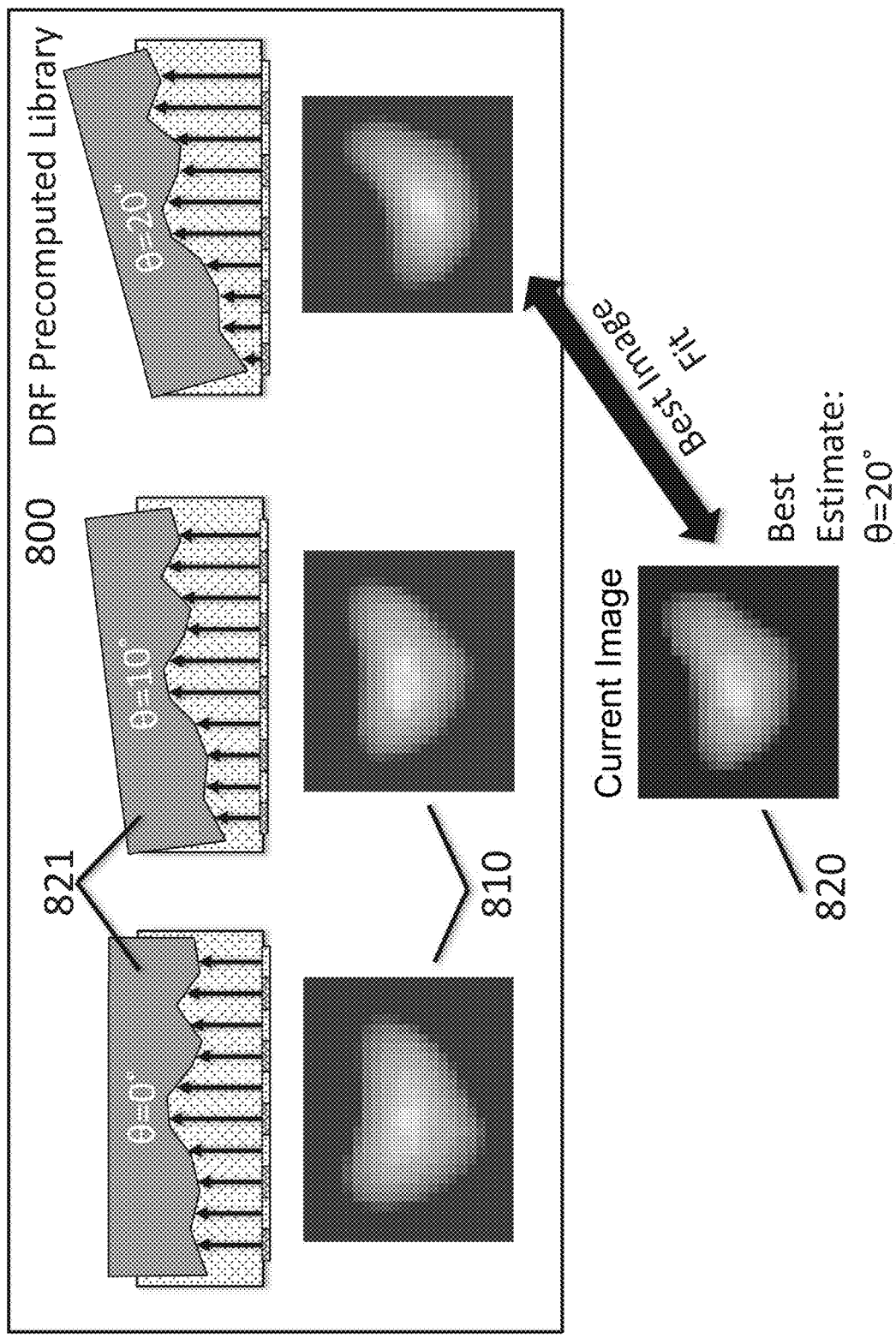
FIG. 8 illustrates the digitally reconstructed force match (DRFM) process by which a digitally reconstructed force simulation library is compared with real-time sensor-derived force distribution to determine the position of the tracked object.

FIG. 8 schematically illustrates the DRFM method for determining the 6DOF position and orientation of the target object in 3D space. Utilizing the force simulation technique described above, the sensor force distributions 810 produced by many different positions and orientations of a targeted object 821 are respectively simulated and stored in a Digitally Reconstructed Force (DRF) library 800. To determine the current position of the target object, the current readings from the force sensor elements 820 are compared to readings stored in the DRF library. The position and orientation of the object that is associated with closest force sensor match in the DRF library are estimated as the current position and orientation of the tracked object. For force sensors arranged in a matrix array configuration, the comparison can utilize known image-based comparison techniques such as cross correlation. In one embodiment, the DRF library image with the highest correlation coefficient to the current force sensor image is selected as the closest match. Note that for simplicity FIG. 8 illustrates matching for only one DOF (θ, or pitch), while the actual implementation of DRFM can match multiple DOF, such as 6 DOF. In some embodiments, interpolation between the DRF library positions and orientations may be used to achieve more accurate positioning of the tracked object. In other words, instead of directly assigning the position and orientation based on the closest cross-correlation match (e.g. θ=0°, 10°, or 20° in FIG. 8), interpolation can be used to assign a position and orientation that is between the discrete values stored in the DRF library (e.g.) θ=18°. Interpolation becomes more important to achieving an accurate result as the "resolution" of the DRF library decreases (e.g. the further the pre-computed positions and orientations are spaced out).

Figure 9B:
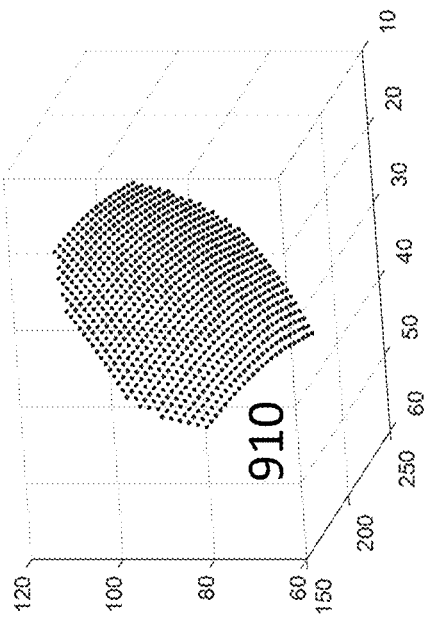
FIGS. 9A-9D show the CPM process by which a force distribution map reflecting the shape of the tracked object is compared with a set of a-priori contours to determine position of the tracked object.

FIGS. 9A-9D show an exemplary PCM method for determining the 6DOF position and orientation of the target object in 3D space. The principle of this method is to generate a estimated 3D point cloud of points on the estimated surface of the tracked object based on the current force sensor readings, then register that point cloud with a second reference point cloud representing the surface geometry of the tracked object. In some embodiments, the force sensor elements are arranged in a matrix array, and their combined readings form a force image 900. Based on the known geometric location of the force sensor array in 3D space, an estimated point cloud 910 of points in 3D space can be generated according to the inverse of the force simulation process previously described, as shown in FIG. 9B. To illustrate this inverse process, consider the case of the linear spring deformable material model. To invert this model and generate a 3D estimated point cloud 910, the distance x from each pixel of the force image (e.g. each force sensor element) to the tracked object is given as: $x=y-F/k$, where F is the force measured on each respective pixel, k is the material spring constant, and y is the resting thickness of the deformable material. The estimated point cloud is generated by projecting a normal vector from the 3D location of each force sensor element (e.g. pixel) and plotting a point along the normal vector at the computed distance x. It is appreciated that if other deformable material models are used (e.g. FEA or others), a different inverse process can be used to generate the 3D estimated point cloud 910. It is further appreciated that the deformable material can be the scalp, an artificial material placed over the force sensor elements, a combination of both, or other elastic materials.

Figure 9D:
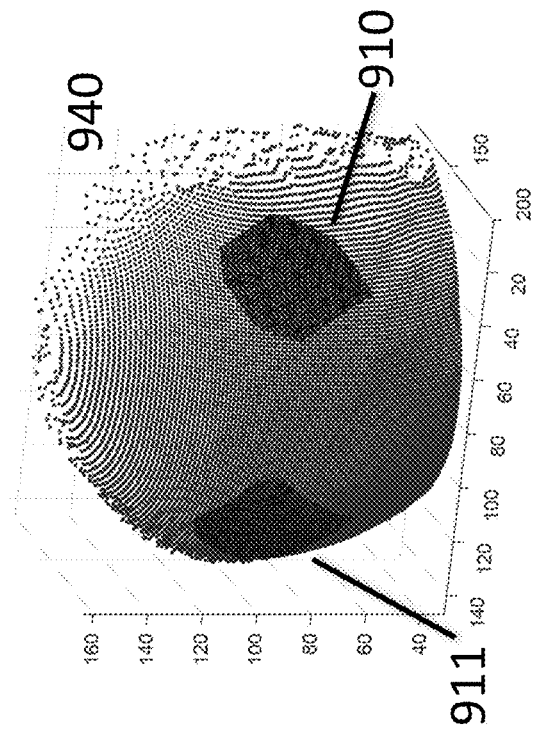
Figure 9A:
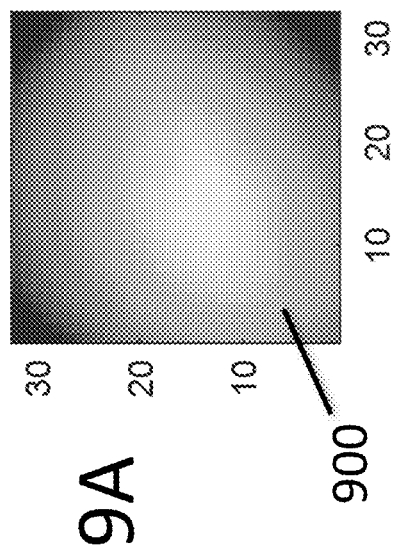
Figure 9C:
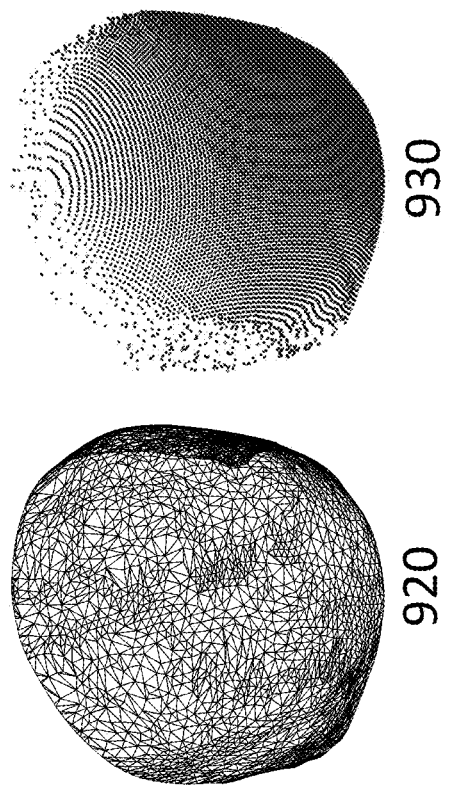

In a separate step of the point cloud matching (PCM) method, as shown in FIG. 9C, a reference point cloud 930 of the tracked object is established. In some embodiments where the tracked object is the skull and a triangle mesh 920 is generated to represent the skull surface, the reference point cloud 930 can be generated by interpolating the vertices of the triangle mesh onto a uniform grid. Once the reference point cloud 930 and the estimated point cloud 910 have been computed, the final step (shown in FIG. 9) is to register them together 940. In some embodiments, rigid point cloud registration methods known in the art are used to register the reference point cloud 930 and estimated point cloud 910 together. The result of this registration 940 is the 6DOF relative position and orientation of the estimated point cloud with respect to the reference point cloud. In one embodiment, if the reference point cloud represents the nominal treatment position in a radiosurgery procedure, registrated with the estimated point cloud gives the 6DOF current position of the skull with respect to the nominal treatment position. In FIG. 9D, two estimated point clouds are shown (one on each side of the skull, 910 and 911). These represent an embodiment where there are two force sensing matrix arrays, one on each side of the patient's head, for example, as shown in FIGS. 12C and 12D. For registration, the estimated point clouds from each of the two respective sensor arrays 910 and 911 are combined into one rigid cloud, and the resulting combined cloud is registered with the reference cloud 930 to compute the 6DOF position of the head with respect to the sensor arrays.

Figure 10B:
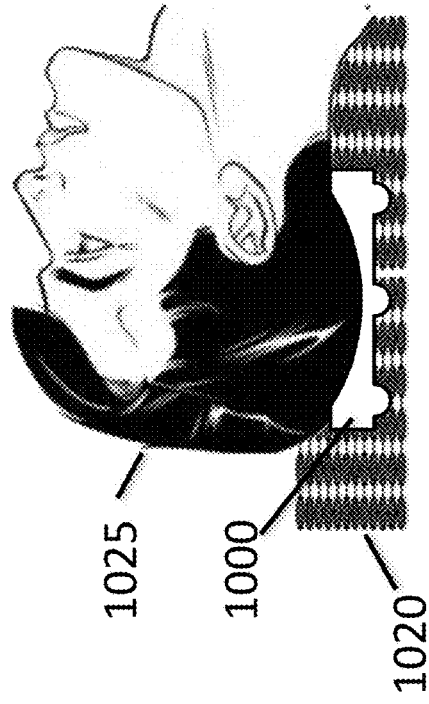
FIGS. 10A-10D describe the CPM method in which the location of protruding objects are sensed by a force measuring array.
Figure 10A:
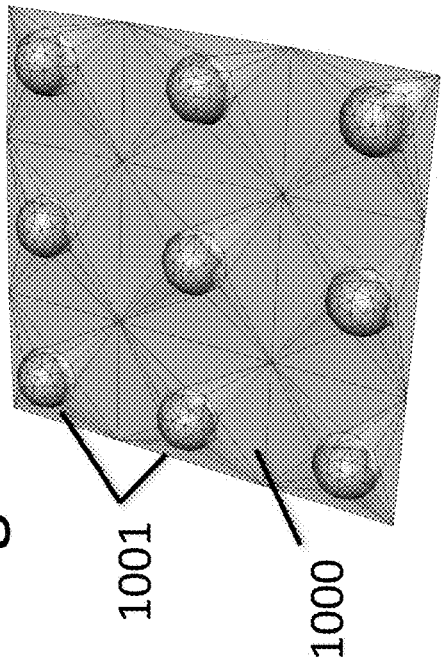
Figure 10D:
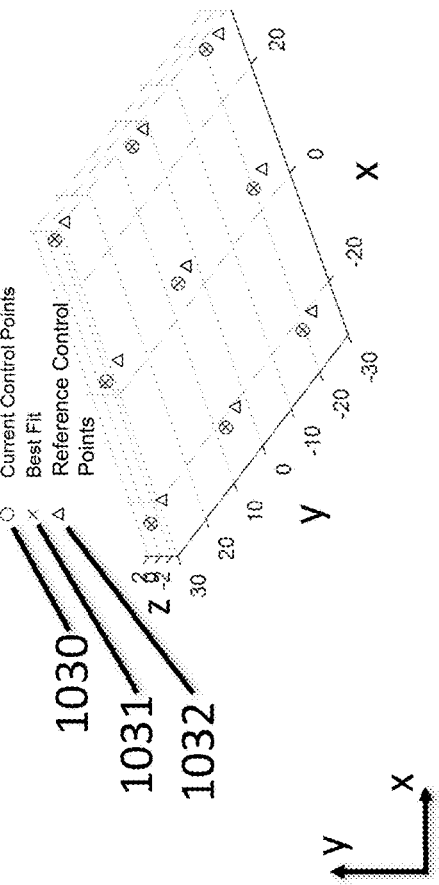
Figure 10C:
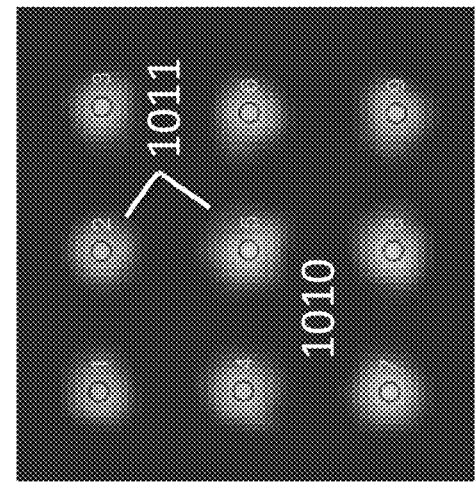

FIGS. 10A-10D show the control point matching (CPM) method for determining the 6DOF position and orientation of a target object (e.g. interface member) in 3D space using force sensing elements. In CPM, the tracked target object 1000 has discrete protruding bumps 1001, or "control points," that activate the elements of a force sensing array in a way that produces easily-detectable peaks 1011 on the array force "image" 1010. In some embodiments, the tracked object's control points 1001 are arranged in a geometrically known pattern, such as that shown in FIG. 10A. For the purposes of tracking patient anatomy, the tracked CPM object can be fixed to the patient in a secure way. For example, for tracking the skull in cranial radiosurgery, an object 1000 with contact geometry as shown in FIG. 10A can be fixed to the back of the patient's head 1025 while resting on a flat force sensing array 1020, as shown in FIG. 10B. As explained previously, the force sensor array 1020 preferably has a deformable material placed over it to provide compliant coupling between the tracked object 1000 and the force sensor elements. FIG. 10C shows the force sensor array image 1010 with nine discrete areas of activation 1011 corresponding to the nine control points on the tracked object 1001. The control point pixel of each activation area in the XY-plane of the force sensor array 1020 may be found by segmenting the respective activation areas from the background, then designating the control point pixel within each area as the geometric mean of the pixels within the area, weighted mean, peak force pixel, or others. The Z-coordinate (out of the force sensor array plane) of the 3D control point may be assigned based on the magnitude of the force within each activation area. The idea is that the deformable material between the sensor array and the tracked object's protruding bumps will exert a force on the sensor array based on the amount the material is deformed under each protruding bump, which corresponds to the Z-coordinate of each bump. As shown in FIG. 10D, once the 3D coordinates of each current control point are determined 1030, they may be plotted in 3D space. The points may then be registered to a reference set of points 1032, which can be based on the known a-priori control point geometry (if tracking in absolute 3D space is desired), or alternatively the control points measured at a previous tracking time (if relative tracking is desired). Control point registration can proceed using methods known in the art such as Horn's Method or any suitable method. The result of the control point registration is a set of best fit points 1031 and a 6DOF transformation that relates the current measured 3D control points 1030 to the reference points 1032 (from the a-priori geometry or previously measured control points), and in turn represents the 6DOF position and orientation of the tracked object 1000.

Figure 11C:
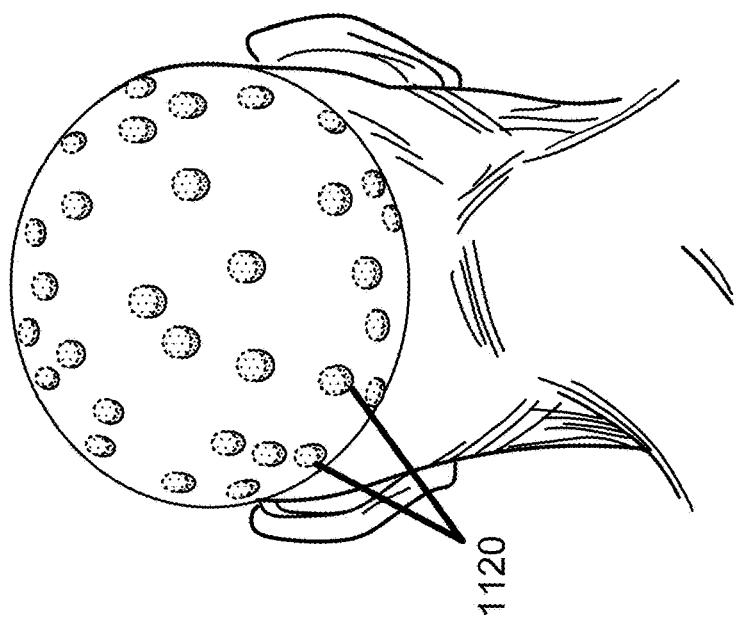
FIGS. 11A-11C illustrate a form of CPM in which the control points are uniquely shaped or spaced and worn on the back of the patient's head.
Figure 11B:
Figure 11A:
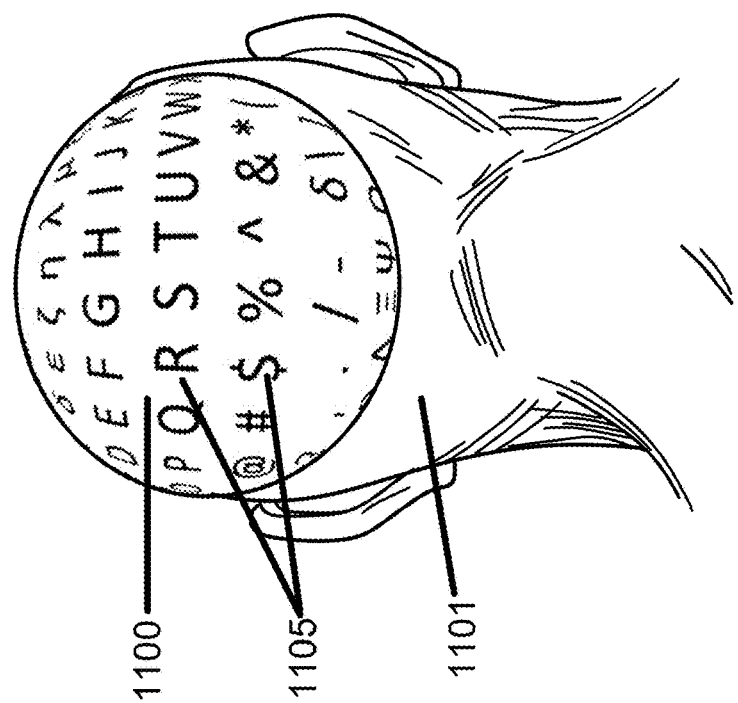

FIG. 11A illustrates a form of CPM in which each of the control point bumps consists of a uniquely shaped raised protrusions 1105 and 1111, worn on the back of the patient's head 1101, for example with a tightly fitting swim-cap like headgear 1100. FIG. 11B shows a close-up cross section of a uniquely shaped raised protrusion 1111 on headgear sample cross-section 1110. In this scenario, the uniquely shaped raised protrusion 1105 will make a distinct pattern of pressure on force sensing matrix, as shown in FIGS. 2 and 10, and the center of each pressure distribution may be considered as a single control point. Movements of the head will result in a different pattern of pressure on the force-sensing matrix that uniquely defines the new head position. A similar approach to CPM is shown in FIG. 11C, where instead of each control point protrusion having a different shape, all of the protrusions 1120 have the same shape, but their relative spacing is unique and encodes the unique position of the patient's head with respect to the force sensing array. These approaches shown in FIGS. 11A-11C may be used within the context of Mode A or B as described in FIG. 2.

FIGS. 12A-12G demonstrate examples of different configurations of the sensor arrays and headrest. FIG. 12A shows a flat sensor array 1206 beneath optional elastic material 1205 and head 1201. FIG. 12B shows a flexible sensor array 1216 beneath head 211 in a curved conformation, with optional interposed elastic material 1215. FIG. 12C shows two arrays 1225 placed beneath 2 roughly diagonal sides of the of head 1221, with optional interposed elastic material 1225. FIG. 12D shows sensor or sensor arrays 1235 in front of head and back of head 1231, with optional interposed elastic material 1236. FIG. 12E shows sensors 1246 and optional interposed elastic material 1245 resting upon linear motion platform 1243, while head 1241 is laterally or circumferentially supported by headrest 1242. FIG. 12F shows sensors 1255 located on a 6 degree-of-freedom moveable support 1253 such as a Gough-Stewart platform with optional interposed elastic material 1356, beneath head 1251 which is otherwise supported by lateral or circumferential headrest 1252. Moveable support 1263 is shown in a partially compressed position in FIG. 12G, as is head 1261, headrest 1262, sensors 1265 and, optional interposed elastic material 1265.

Throughout this application, whenever reference is made to 6 DOF tracking or positioning, it can be assumed that tracking or positioning of fewer than 6DOF (for example, 3DOF or 4DOF) may also be implemented under the general methods, devices, and embodiments described. Furthermore, tracking of more than 6DOF may also be possible if multiple connected rigid bodies are tracked, or deformable bodies are tracked It is appreciated that the methods and processes described herein can be embodied in programmable instructions recorded on a tangible memory of a processor in a computing unit of the tracking systems described herein. Such tracking systems can be separate from or incorporated within the computing units of any associated radiation treatment system. It is further appreciated that the methods and processes described herein can be performed automatically or that certain steps can be performed in response to input commands from the clinician or surgeon, as needed.

It should also be noted that while most scenarios discussed in this application relate to tracking and positioning a patient's head for the purposes of stereotactic radiosurgery, other medical and non-medical positioning and tracking applications are also enabled by the disclosed methods and devices, including computerized image-guided surgical systems, other image-guidance systems, robotic medical devices and stereotactic positioning systems.

While the exemplary embodiments have been described in some detail, by way of example and for clarity of understanding, those of skill in the art will recognize that a variety of modification, adaptations, and changes may be employed. Hence, the scope of the present invention should be limited solely by the appending claims.

In the foregoing specification, the invention is described with reference to specific embodiments thereof, but those skilled in the art will recognize that the invention is not limited thereto. Various features, embodiments and aspects of the above-described invention can be used individually or jointly. Further, the invention can be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art.

What is claimed is:

1. A method of tracking motion of a rigid portion of a patient's body for medical treatment, the method comprising:
    determining a force or pressure distribution from one or more force sensors interfaced, directly or indirectly, with a portion of the patient's body having a targeted tissue;
    determining a change from an initial position of the portion of the patient's body, in which the targeted tissue is aligned with a radiation treatment beam from a radiosurgery system, by detecting a change in the force or pressure distribution detected with the one or more force sensors;
    determining an updated position of the portion of the patient's body having the targeted tissue; and
    re-aligning the radiation treatment beam with the targeted tissue in the updated position,
    wherein the one or more force sensors comprise at least one strain gauge extending between a treatment mask and a patient support, wherein each strain gauge of the at least one strain gauge is electrically supported by a Wheatstone quarter-bridge circuit such that an output voltage is indicative of a deformation of the respective strain gauge corresponding to the change from the initial position.

2. The method of claim 1, wherein the medical treatment is stereotactic delivery of radiation.

3. The method of claim 1, wherein the one or more force sensors comprise any of or any combination of:
    piezoelectric, resistive, capacitive, optical, pneumatic, and hydraulic sensors.

4. The method of claim 1, wherein the one or more force sensors comprise a plurality of force sensors.

5. The method of claim 4, wherein the plurality of force sensors are arranged in an array disposed beneath or at least partly extending about the portion of the patient's body.

6. The method of claim 4, wherein the plurality of force sensors are engaged with the portion of the patient's body through an interface member having one or more pre-defined shaped features at known locations on the interface member to improve detection of force by the one or more force sensors.

7. The method of claim 4, wherein the plurality of force sensors are arranged in array and incorporated within a pad supporting the portion of the patient's body.

8. The method of claim 1, wherein the portion of the patient's body is a head of the patient.

9. The method of claim 1, wherein re-aligning the radiation treatment beam comprises adjusting a trajectory of the radiation treatment beam or adjusting a patient support.

10. The method of claim 1, wherein detecting the change in the force or pressure distribution comprises the detection exceeding a pre-defined threshold.

11. The method of claim 10, further comprising:
    outputting a notification indicating the change from the initial position of the portion of the patient's body.

12. The method of claim 1, wherein determining an updated position of the portion of the patient's body comprises utilizing an imaging procedure native to the radiosurgery system.

13. The method of claim 1, wherein the one or more force sensors comprise a plurality of force sensors disposed within an array, and wherein determining the updated position of the portion of the patient's body is based, at least partly, on a detection output from the plurality of force sensors disposed within the array.

14. The method of claim 13, wherein determining the updated position further comprises determining a position and orientation of the portion of the patient's body based on an output of force magnitude from each of the plurality of force sensors.

15. The method of claim 14, wherein determining the updated position is further based on relative positions of the plurality of force sensors within the array.

16. The method of claim 1, wherein the portion of the patient's body comprises the patient's head, and the one or more force sensors comprise a plurality of force sensors, and wherein determining the updated position of the portion of the patient's body is based, at least partly, on a detection output from the plurality of force sensors, and wherein the plurality of sensors are disposed within any of:
    a substantially flat sensor array beneath the patient's head;
    a flexible sensor array that is sufficiently flexible to accommodate a curvature of the patient's head when rested thereon;
    at least two arrays placed along diagonal sides of the patient's head;
    at least two arrays placed along a front and a back of the patient's head;
    a sensor array with interposed elastic material between the sensor array and the patient's head;
    a sensor array resting upon a linear motion platform;
    a sensor array disposed on a movable support;
    a sensor array disposed on a compressible support; or
    any combination thereof.

17. The method of claim 1, wherein the one or more force sensors comprise a plurality of force sensors, each extending between the portion of the patient's body and the patient support, wherein the plurality of force sensors are positioned to detect forces in differing directions from which the updated position is determined.

18. The method of claim 1, wherein the at least one strain gauge comprises a plurality of strain gauges, each extending between the portion of the patient's body and the patient support, wherein each of the plurality of strain gauges are positioned to detect strain in differing directions from which the updated position is determined.

19. A method of tracking motion of a rigid portion of a patient's body for medical treatment, the method comprising:
    determining a force or pressure distribution from one or more force sensors interfaced, directly or indirectly, with a portion of the patient's body having a targeted tissue;
    determining a change from an initial position of the portion of the patient's body, in which the targeted tissue is aligned with a radiation treatment beam from a radiosurgery system, by detecting a change in the force or pressure distribution detected with the one or more force sensors;
    determining an updated position of the portion of the patient's body having the targeted tissue; and re-aligning the radiation treatment beam with the targeted tissue in the updated position, wherein determining an updated position of the portion of the patient's body comprises utilizing an imaging procedure native to the radiosurgery system, wherein determining the updated position of the portion of the patient's body comprises obtaining a radiographic image that is matched to a digitally reconstructed radiograph (DRR) image.

20. A method of tracking motion of a rigid portion of a patient's body for medical treatment, the method comprising:

determining a force or pressure distribution from one or more force sensors interfaced, directly or indirectly, with a portion of the patient's body having a targeted tissue;

determining a change from an initial position of the portion of the patient's body, in which the targeted tissue is aligned with a radiation treatment beam from a radiosurgery system, by detecting a change in the force or pressure distribution detected with the one or more force sensors;

determining an updated position of the portion of the patient's body having the targeted tissue; and re-aligning the radiation treatment beam with the targeted tissue in the updated position, wherein the one or more force sensors comprise a plurality of force sensors disposed within an array, and wherein determining the updated position of the portion of the patient's body is based, at least partly, on a detection output from the plurality of force sensors disposed within the array, wherein determining the updated position further comprises determining a position and orientation of the portion of the patient's body based on an output of force magnitude from each of the plurality of force sensors, wherein determining the updated position is further based on relative positions of the plurality of force sensors within the array, wherein the array of the plurality of force sensors is incorporated within or disposed on a deformable material, and wherein determining the updated position is further based on a material property of the deformable material.

21. A method of tracking motion of a rigid portion of a patient's body for medical treatment, the method comprising:

determining a force or pressure distribution from one or more force sensors interfaced, directly or indirectly, with a portion of the patient's body having a targeted tissue;

determining a change from an initial position of the portion of the patient's body, in which the targeted tissue is aligned with a radiation treatment beam from a radiosurgery system, by detecting a change in the force or pressure distribution detected with the one or more force sensors;

determining an updated position of the portion of the patient's body having the targeted tissue; and re-aligning the radiation treatment beam with the targeted tissue in the updated position, wherein the one or more force sensors comprise a plurality of force sensors disposed within an array, and wherein determining the updated position of the portion of the patient's body is based, at least partly, on a detection output from the plurality of force sensors disposed within the array, wherein determining the updated position further comprises determining a position and orientation of the portion of the patient's body based on an output of force magnitude from each of the plurality of force sensors, wherein determining the updated position is further based on relative positions of the plurality of force sensors within the array, wherein the array of the plurality of force sensors is incorporated within or disposed on a deformable material, and wherein determining the updated position is further based on a material property of the deformable material, wherein determining the updated position utilizes a mechanics model as a function of the output of force magnitude from each of the plurality of force sensors, the relative positions of the plurality of force sensors within the array, and the material property of the deformable material.

22. A method of tracking motion of a rigid portion of a patient's body for medical treatment, the method comprising:

determining a force or pressure distribution from one or more force sensors interfaced, directly or indirectly, with a portion of the patient's body having a targeted tissue;

determining a change from an initial position of the portion of the patient's body, in which the targeted tissue is aligned with a radiation treatment beam from a radiosurgery system, by detecting a change in the force or pressure distribution detected with the one or more force sensors;

determining an updated position of the portion of the patient's body having the targeted tissue; and re-aligning the radiation treatment beam with the targeted tissue in the updated position, wherein the one or more force sensors comprise a plurality of force sensors disposed within an array, and wherein determining the updated position of the portion of the patient's body is based, at least partly, on a detection output from the plurality of force sensors disposed within the array, wherein determining the updated position comprises performing a digitally reconstructed force matching (DRFM) procedure comprising:

obtaining a current force output or pressure distribution from the one or more force sensors;

comparing the current force output or pressure distribution to pre-defined force outputs or pressure distributions corresponding to a plurality of differing positions and orientations of the portion of the patient's body; and determining a current position and orientation of the portion of the patient's body based on the comparison.

23. A method of tracking motion of a rigid portion of a patient's body for medical treatment, the method comprising:

determining a force or pressure distribution from one or more force sensors interfaced, directly or indirectly, with a portion of the patient's body having a targeted tissue;

determining a change from an initial position of the portion of the patient's body, in which the targeted tissue is aligned with a radiation treatment beam from a radiosurgery system, by detecting a change in the force or pressure distribution detected with the one or more force sensors;

determining an updated position of the portion of the patient's body having the targeted tissue; and re-aligning the radiation treatment beam with the targeted tissue in the updated position, wherein the one or more force sensors comprise a plurality of force sensors disposed within an array, and wherein determining the updated position of the portion of the patient's body is based, at least partly, on a detection output from the plurality of force sensors disposed within the array, wherein determining the updated position comprises performing a point cloud matching (PCM) procedure comprising:

generating a 3D point cloud of an estimated surface of the portion of the patient's body based on a current output from the one or more force sensors;

determining a reference point cloud of the portion of the patient's body; and registering the generated 3D point cloud and the reference point cloud together to determine a 6 degree-of-freedom (DOF) current position and orientation of the portion of the patient's body.

24. The method of claim 13, A method of tracking motion of a rigid portion of a patient's body for medical treatment, the method comprising:

determining a force or pressure distribution from one or more force sensors interfaced, directly or indirectly, with a portion of the patient's body having a targeted tissue;

determining a change from an initial position of the portion of the patient's body, in which the targeted tissue is aligned with a radiation treatment beam from a radiosurgery system, by detecting a change in the force or pressure distribution detected with the one or more force sensors;

determining an updated position of the portion of the patient's body having the targeted tissue; and re-aligning the radiation treatment beam with the targeted tissue in the updated position, wherein the one or more force sensors comprise a plurality of force sensors disposed within an array, and wherein determining the updated position of the portion of the patient's body is based, at least partly, on a detection output from the plurality of force sensors disposed within the array, wherein the determining the updated position comprises performing a control point matching (CPM) procedure comprising:

determining a force image from force outputs of the plurality of force sensors such that each sensor corresponds to a pixel of the force image; and registering the force image to a reference set of points based on a pre-defined control geometry to determine a current position and orientation of the portion of the patient's body.

* * * * *